US007001180B2

(12) United States Patent
Bass

(10) Patent No.: US 7,001,180 B2
(45) Date of Patent: Feb. 21, 2006

(54) ORTHODONTIC APPLIANCE

(75) Inventor: Neville M. Bass, London (GB)

(73) Assignee: Dynamax (UK) Limited, London (GB)

( * ) Notice: Subject to any disclaimer, the term of this patent is extended or adjusted under 35 U.S.C. 154(b) by 108 days.

(21) Appl. No.: 10/299,015

(22) Filed: Nov. 19, 2002

(65) Prior Publication Data

US 2003/0124479 A1 Jul. 3, 2003

(30) Foreign Application Priority Data

Nov. 20, 2001 (GB) .................................. 0127821

(51) Int. Cl.
A61C 7/00 (2006.01)
(52) U.S. Cl. .......................................... 433/19; 433/18
(58) Field of Classification Search ................. 433/19, 433/18, 24, 21, 22, 6; 128/848
See application file for complete search history.

(56) References Cited

U.S. PATENT DOCUMENTS

| 4,354,833 A | 10/1982 | Fujita |
| 4,597,738 A | 7/1986 | Sander et al. |
| 4,618,324 A | 10/1986 | Nord |
| 4,708,646 A | 11/1987 | Jasper |
| 4,752,222 A | 6/1988 | Bass |
| 5,324,196 A | 6/1994 | Magill |
| 5,376,001 A | 12/1994 | Tepper |
| 5,848,891 A | 12/1998 | Eckhart et al. |
| 6,099,304 A | 8/2000 | Carter |
| 6,394,799 B1 | 5/2002 | Testa et al. |

FOREIGN PATENT DOCUMENTS

| DE | 3618505 | 12/1987 |
| DE | 29501405 | 5/1995 |
| DE | 19535170 | 2/1996 |
| EP | 0128744 | 12/1984 |
| EP | 0312884 | 4/1989 |
| FR | 2760631 | 9/1998 |
| WO | 9604864 | 2/1996 |
| WO | 0001317 | 1/2000 |

OTHER PUBLICATIONS

Great Britain Search Report, dated Apr. 30, 2003.

Primary Examiner—Cary E. O'Connor
Assistant Examiner—Candice C. Stokes
(74) Attorney, Agent, or Firm—Baker Botts, LLP

(57) ABSTRACT

Orthodontic appliance for limiting relative longitudinal movement between the upper and lower jaws to correct malocclusions and/or to prevent snoring. The appliance includes a first component for engaging the upper jaw, and a second component for engaging the lower jaw. A projection is provided on one of the first and second components to abut the other of the first and second components, laterally offset from the jaws.

52 Claims, 4 Drawing Sheets

ORTHODONTIC APPLIANCE

The present invention relates to an orthodontic appliance and to components for forming such an appliance. In particular, the present invention relates to an orthodontic appliance used to correct a malocclusion in which one of the upper and lower jaws protrudes excessively or is positioned further back with respect to the other jaw. Further, the appliance of the present invention, by holding the lower jaw forward, is useful in preventing snoring, in the treatment of sleep apnoea and in the treatment of mandibular joint problems.

To treat a malocclusion in which the lower jaw recedes excessively with respect to the upper jaw, it is desirable to encourage the patient to hold the receding lower jaw forward. It is known to provide an orthodontic appliance that either encourages the patient to hold their jaw forward, by making it uncomfortable for the patient to allow the jaw to assume its normal, retracted, position, or which prevents the patient from allowing their jaw to assume its normal, retracted position. This alters the growth of the jaw, and the jaw thereby tends to assume the forward position naturally. Further, the muscles holding the jaw may also be strengthened by holding the forward posture.

Ideally, the orthodontic appliances that are used to treat such malocclusions are adjustable. In this way, the patient can be encouraged initially to hold their receding jaw a short way forward, with the amount of forward movement being increased during the course of treatment as the muscles of the jaw strengthen and growth takes place. This is preferable to seeking to encourage all the forward movement in a single step and may promote better jaw growth.

It is preferred that the orthodontic appliance does not exert undue pressure on the teeth of the patient, since this may act to move the teeth within the jaw, rather than or in addition to moving the jaw.

One form of known orthodontic appliance for correction of misalignment of the jaws comprises a housing that is attached or connected to the upper teeth of the patient, typically being mounted on the inside of the rear teeth. An arm extends from the housing in line with one side of the patient's mouth, the arm terminating in a lingual pad. The pad is designed to contact the inside of the lower jaw of the patient. In this case, the patient, is encouraged to move their lower jaw forward to avoid contact between the inside of the lower jaw and the lingual pad. The patient is not prevented from retracting their lower jaw, however if the lower jaw is retracted this will contact the lingual pad and cause the patient some discomfort. It is known that the appliance can be adjusted to advance the position of the lingual pad, thereby encouraging the patient to progressively move their lower jaw further forward. Examples of such appliances may be found in my earlier British Patent Application No. GB-A-2192339 and International Patent Application No. WO 95/03005.

Another form of orthodontic appliance that is used to treat malocclusions of the type referred to above is the "Clark Twin Block" device. This comprises two mouldings, one designed to fit over the teeth of the upper jaw and the other designed to fit over the teeth of the lower jaw. The mouldings each include a block that, in use, project towards the other moulding. In use, the blocks will extend between the teeth of the upper jaw and the corresponding teeth of the lower jaw. The blocks on the respective mouldings are offset. Where the appliance is used to cause the patient to move their lower jaw forward, the blocks are located on the upper and lower mouldings such that, in the desired position of the upper and lower jaws, the front surface of the block on the upper moulding is aligned with the rear surface of the block on the lower moulding. In this way, when the patient moves their lower jaw forward and closes their mouth, the lower jaw is, prevented from reverting to its retracted position as the blocks on the upper and lower mouldings come into contact and prevent rearward movement of the lower jaw. Typically, the front of the block on the upper moulding and the rear of the block of the lower moulding are inclined with respect to each other. This assists the correct positioning of the jaws during the opening and closing of the mouth.

The Clark Twin Block devices have a number of disadvantages. Since the appliance is formed from two mouldings, each, having a block which must co-operate to ensure the correct positioning of the jaws, the device is not adjustable. Therefore, to construct the devise, it is necessary to take mouldings of the existing bite of the patient and to determine the desired final bite. The device must then be formed based on these mouldings. It is not possible to make adjustments of the device when this is fitted in the patient's mouth, and therefore the device must accurately be formed. Further, as the device cannot be adjusted easily, either a number of appliances must be made for a patient as their jaws are gradually moved to the desired position, or the device is made to encourage movement of the jaws in a single step. The only way to adjust the device is by removing the device from the patient's mouth, and adding material to the blocks. This would often require returning the device to a laboratory. A further problem with the appliance is that the solid mouldings covering both the upper and lower teeth of the patient prevent the teeth from growing together properly and results in a gap between upper and lower back teeth. Further, the use of the appliance tends to increase the dimension of the lower part of the face, which is undesirable in many cases. Therefore, the use of the device may cause other problems. A yet further problem with the device is that the blocks will become disengaged when the patient's mouth is opened. Therefore, the jaws will return to their natural position when the patient opens his or her mouth. Whilst it would be possible to increase the height of the blocks to prevent the blocks becoming disengaged in this way, since the blocks are positioned between the upper and lower teeth, the upper and lower teeth must be held apart by an amount sufficient to accommodate the blocks. This is undesirable. It is particularly undesirable to increase the size of the blocks, and therefore the space that needs to be maintained between the teeth of the upper and lower jaw.

Another form of appliance is the "Herbst" appliance. This comprises an upper jaw part and a lower jaw part for fixing to the teeth of the upper and lower jaw respectively. Pivotally attached to one of the upper and lower jaw parts is a rod which is slidably received within a tubular member pivotally mounted to the other part of the appliance. An adjustable stop is provided within the tubular member to limit the movement of the rod into the tubular member.

This device is complex to construct, and, due to the number of moving components, is particularly susceptible to damage.

Other devices that hold the lower jaw forward are made in one piece which makes them more difficult for the patient to use and affects the speech significantly.

Other devices are known in which a prong extends from an upper jaw member to the lower jaw at the front of the mouth, which is unsightly and interferes with speech.

The above examples have been described with reference to a desire to move the lower jaw forward with respect to the upper jaw. However, it will be understood that it may be necessary to move the upper jaw forward with respect to the lower jaw. In this case, suitable modification of the components of the appliance will be required.

According to a first aspect of the present invention, an orthodontic appliance arranged to hold one of the upper and lower jaw in a forward position includes:
a first component for engaging the upper jaw;
a second component for engaging the lower jaw;
at least one of the first and second components including a fixed projection arranged to abut the other of the first and second components, the fixed projection being arranged so that, in use, the abutment between the components is offset laterally from the left and right side of the jaws towards the back of the mouth and restricts the relative longitudinal movement of the upper and lower jaw in one direction.

With the present invention, components engage the upper and lower jaws of a patient, and the components are arranged to abut with each other to limit the relative backward or forward movement between the jaws. This therefore achieves the primary function of the appliance. The abutment between the components engaging the upper and lower jaws occurs in a space laterally offset from the teeth in the patient's mouth. This is in contrast to the prior art in which the abutment occurs between blocks between the upper and lower teeth. Therefore, unlike the prior art, the present arrangement does not require the upper and lower jaws to be spaced apart further than normal. By providing the abutment means towards the, rear of the patient's mouth, closer to the hinge point between the upper and lower jaws, the amount of movement between the upper and lower jaws when the patient opens his or her mouth at the point of abutment is less than towards the front of the mouth. Therefore, the abutment between the upper and lower jaw engaging components may be maintained more easily during opening of the mouth. Therefore, unlike the prior art, the forward positioning of the jaws may be maintained even when the mouth is opened. The provision of a fixed projection, rather than a pivotally connected rod or tubular element greatly improves the simplicity of the device, thereby reducing its cost and increasing its reliability.

Although the abutment between the components may be between the outside of the jaw and the inside of the cheek, this may be uncomfortable. Accordingly, it is preferred that the abutment occurs between the left and right sides of the jaw.

An important advantage of providing the abutment between the left and right sides of the jaw is that there is a greater depth between the sides of the jaw than between the outside of the jaw and the cheek. This allows a longer projection where the abutment is provided between the left and right sides of the jaw than where the abutment is provided between the outside of the jaw and the cheek. It is advantageous to have a longer projection, since this can permit the continued abutment between the components over a greater range of opening of the jaws. For example, where only a short projection is provided, when the user opens his or her mouth, the projection will come out of engagement with the other component, and longitudinal movement of the jaws will not be restricted. Where a longer projection is provided, the projection will remain in abutment with the other component when the mouth is opened, and therefore the relative, longitudinal movement of the jaws will remain restricted. Advantageously, the projection has a length of at least 1 cm, and preferably up to about 2 cm.

It is preferred that the projection provided for abutment of the two components has some resilience. In this way, when the patient tries to move the lower jaw relative to the upper jaw to abut the components, the patient will feel some resilience. This is pleasurable to the patient and will therefore encourage the patient to use the appliance. Further, the movement of the jaws against the resilience of the abutment will assist in strengthening the muscles of the jaw.

Advantageously, the resilience may be achieved by forming the projection or the abutment surface of a resilient material. A resilient projection may be in the form of a wire, which is preferably bent to provide the required resilience.

Preferably, the appliance is adjustable such that the relative position of the upper and lower components at which they abut can be adjusted. This may be achieved by displacement of the projection or abutment surface. Such displacement may be arranged by movement of the projection with respect to the jaw engaging component on which it is provided, for example by providing a number of location points for the projection on the jaw engaging component, or by providing an adjustable interconnection between the projection and the jaw engaging component. However, it is preferred that the projection remains fixed to the jaw engaging member, and is bent or otherwise adjusted. This is especially suitable where the projection is formed from a wire or strip of deformable material, such as a stainless steel wire. This provides a simple method for adjustment of the device.

It is preferred that one or both of the jaw engaging components is laterally resilient. This has the advantage that the component may be laterally compressed to assist the placement of the component within the mouth of the patient. Further, the resilience may assist in laterally expanding the jaw to avoid a cross bite developing as the wider part of the lower jaw comes forward. The lateral resilience may be provided by forming the component in a number of separate pieces, some or all of which are resiliently biased with respect to each other. The resilience may be provided by the inclusion of any means for separating the components, and may include a threaded element that may be adjusted to separate the components. Alternatively or additionally, the component may be formed from a resilient material. In a preferred example, the resilience is provided by a wire or strip formed of resilient material. In a particularly preferred embodiment, the component is formed from a multi-piece moulding, the pieces of which are connected by a resilient wire to provide the resilience required. Where the abutment projections are formed from wire, it is preferred that the wire joining the parts of the component extend to form the projections. In this case, the wire includes a central portion for connecting the pieces forming the jaw engaging component, a portion for fixing the wire to the pieces forming the jaw engaging component, and portions forming the projections from the jaw engaging component for abutting the other jaw engaging component. Preferably, the wire may be moulded into the parts forming the jaw engaging component. In this case, the portion for fixing the wire to the parts of the jaw engaging component may include a bent length to give a large length and area for connection between the wire and the jaw engaging component.

Advantageously, two projections are provided for abutting an abutment surface towards either side of the jaw.

The jaw engaging components advantageously engage at least half of the teeth present of the respective upper or lower jaw. This ensures not too much force is applied to individual teeth which could otherwise cause the teeth to move relative to the jaw.

In another aspect of the present invention, a wire for use in forming an orthodontic appliance according to the first aspect of the present invention includes a central portion for connecting the pieces forming the jaw engaging component, a portion for fixing the wire to the pieces forming the jaw engaging component, and portions forming the projections from the jaw engaging component for abutting the other jaw engaging component.

One or both jaw engaging components may include bands for encircling one or more teeth on the jaw. This acts to provide a secure anchorage point to the jaw. Alternatively, one or both of the jaw engaging components is removable, allowing the user to remove the appliance. This is particularly useful when the user wishes to eat, at which time the appliance may hinder eating, or when the user wishes to clean their teeth.

The invention also covers methods of preventing snoring and correcting malocclusions using the device.

The present invention will now be described, by way of example, with reference to the following drawings, in which.

In this description, reference will be made to an "upper" jaw engaging component and a "lower" jaw engaging component. It will be understood that, whilst preferred, the upper and lower components are not limited to act upon the upper and lower jaws respectfully, but instead the upper jaw engaging component could engage the lower jaw, and the lower jaw engaging component could engage the upper jaw. Similarly, the description below relates to an arrangement in which the lower jaw is to be held in a forward position compared to the normal position of the jaw. It will, however, be understood that with minor modifications the system can hold the lower jaw in a rearward or retracted position.

Figure 1:
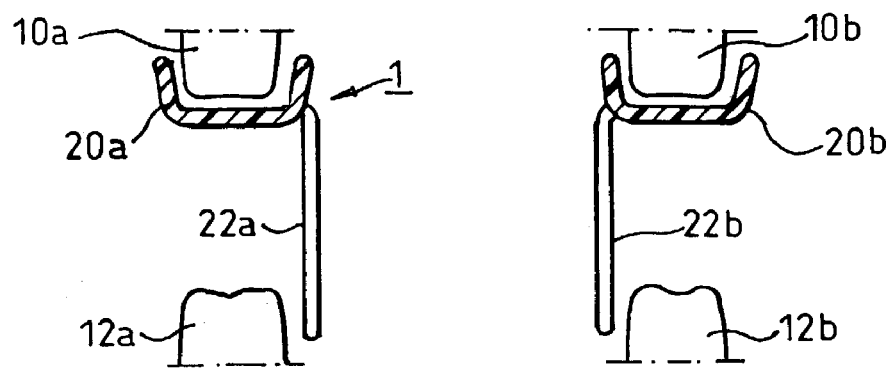
FIG. 1 shows a cross sectional view from the front of an upper jaw engaging component and the upper and lower teeth of a patient.
Figure 2:
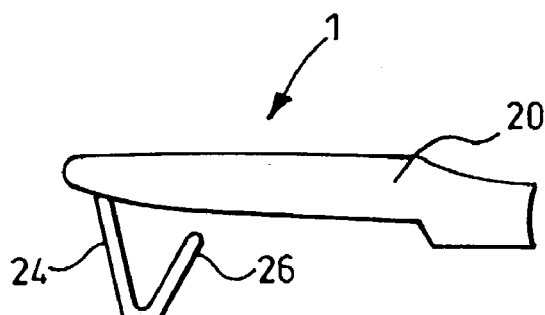
FIG. 2 shows a side view of the upper jaw engaging component of FIG. 1.
Figure 3:
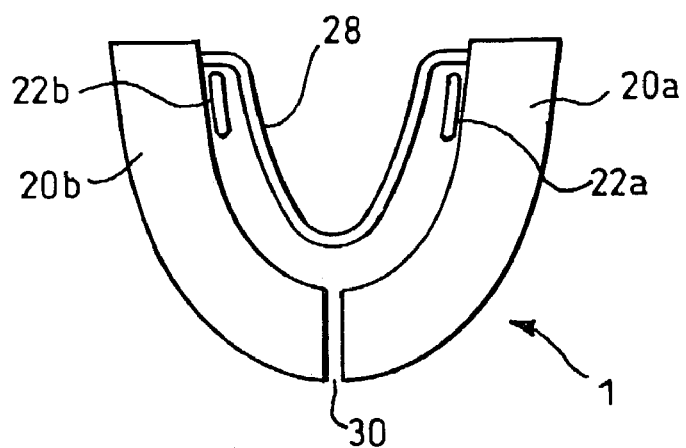
FIG. 3 shows a view from below of the upper jaw engaging component of FIG. 2.
Figure 4:
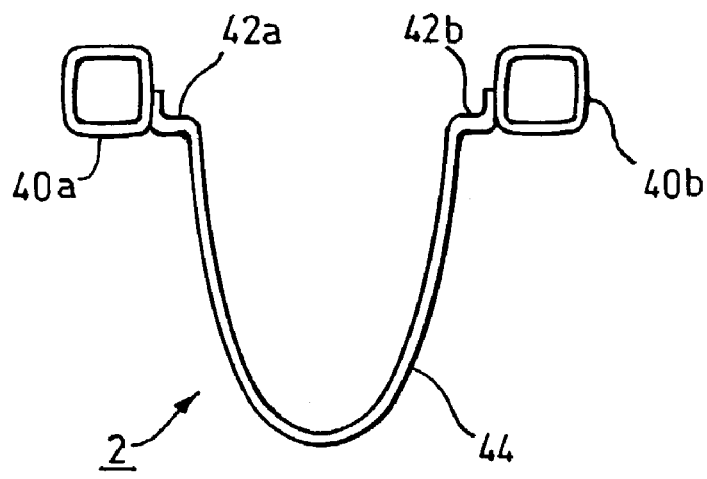
FIG. 4 shows a plan view of one example of a lower jaw engaging component.

In a first example, the orthodontic appliance comprises an upper jaw engaging component 1 shown in FIGS. 1 to 3 and a lower jaw engaging component 2, examples of which are shown in FIGS. 4 and 5.

The upper jaw connecting component 1 includes a moulding 20 that is moulded to the shape of the teeth in the upper jaw of the patient to be treated. Depending from the moulding 20 on each side are projections 22a, 22b. As can be seen in FIG. 1, when the moulding 20 is positioned over the upper teeth 10 of the patient, the projections 22a, 22b extend to a position in the lateral space between the lower teeth 12 of the patient. In this way, the projections 22a, 22b do not contact the top of the lower teeth 12, and therefore do not inhibit the closing of the mouth of the patient.

The moulding contacts all of the teeth present in the patient's upper jaw. The forces resulting from the use of the appliance therefore act upon all teeth of the upper jaw. However, the upper component could be arranged to contact fewer teeth, for example six of the twelve teeth of a full upper jaw. This may still be sufficient to avoid the forces acting on individual teeth to move these relative to the jaw.

As best seen from the side view of FIG. 2, the projections 22 each comprise a generally V-shaped length of resilient wire, for example formed from stainless steel. The wire includes a first portion 24 extending from the moulding 20, and a free end 26. The free end 26 can be bent with respect to the first portion 24 to adjust the appliance as will be described below. The projection 22 has resilience that is also of advantage as will also be described below.

As shown in the underside view of FIG. 3, the moulding 20 is formed in two parts 20a and 20b that are separated by a gap 30. The wire forming the two projections 22a, 22b is a continuous wire that connects the two parts 20a, 20b of the moulding. The wire, being resilient, acts to bias the parts of the moulding apart. This acts to apply pressure to the upper jaw to laterally spread this.

Figure 11:
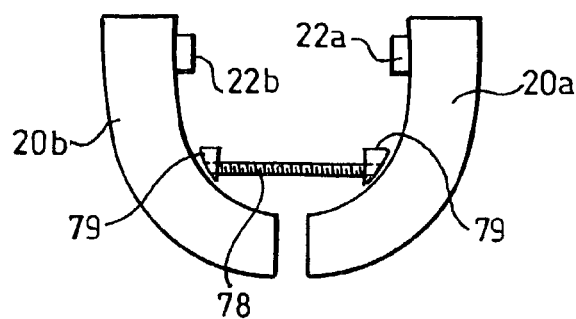
FIG. 11 shows an alternative embodiment of an upper jaw engaging component.

In an alternative embodiment shown in FIG. 11, a threaded component 78 is provided between the parts of the moulding to separate these. By adjustment of the threaded component 78, for example by screwing this into or out of the moulding, or by moving spacers 79 along the threaded component 78 to abut against the parts of the moulding, the lateral spacing of the parts of the moulding can be adjusted to provide the required lateral pressure to the jaw.

In some applications, for example where the appliance is used to prevent snoring, it is undesirable to apply a force that acts to spread the upper jaw. In this case, an alternative upper jaw engaging component may be provided in a single piece.

Figure 6A:
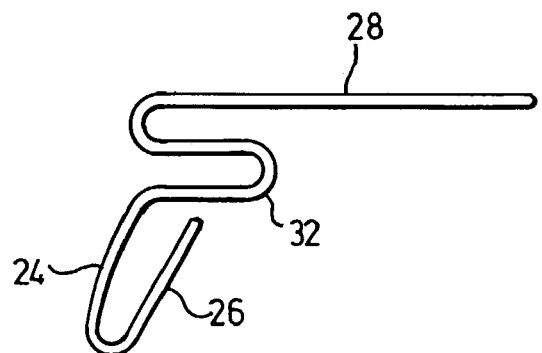
FIGS. 6a–6b show a support means for an upper jaw engaging component.
Figure 6B:
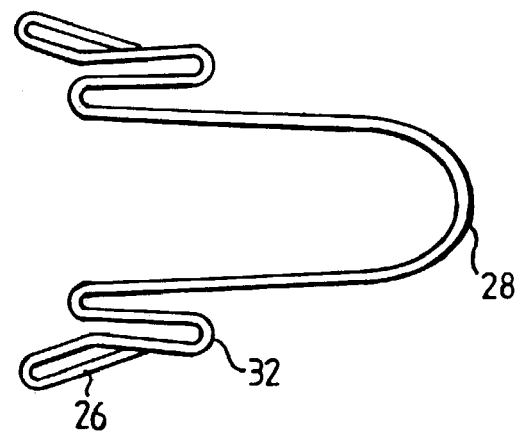

The wire is best shown in FIG. 6a showing a side view and FIG. 6b showing a plan view. As can be seen, this includes the projections 22 including the free ends 26 and first portions 24, a portion 32 for anchoring within the moulded portion 20, and a generally U-shaped portion linking the two sides of the component which in use extends between and resiliently biases the two parts of the moulding 20.

A lower jaw engaging component 2 is shown in plan view in FIG. 4. This component includes two bands 40a, 40b that are designed to fit over teeth on the left and right sides respectively of the lower jaw, thereby anchoring the lower jaw engaging component 2 with respect to the lower jaw. The bands are linked by a generally U-shaped wire, that is shaped to follow the line of the lower jaw. By contacting at least half, and preferably more, of the teeth of the lower jaw, it is ensured that the forces do not act on individual teeth to cause these to move relative to the jaw. Adjacent the bands 40a, 40b, the wire includes shoulders 42a and 42b respectively. In use, these shoulders 42a, 42b will be located in the lateral space between the teeth on the left and right sides of the lower jaw.

Figure 5A:
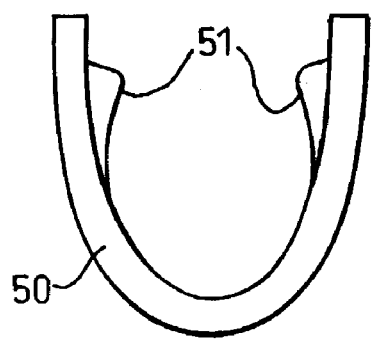
FIGS. 5a–5c show views of an alternative lower jaw engaging component.
Figure 5B:
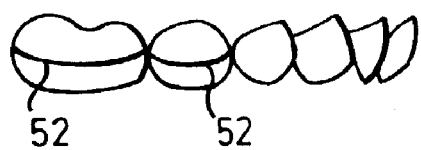
Figure 5C:
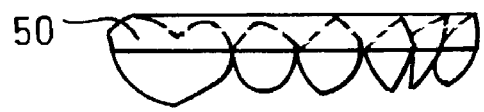

FIGS. 5a to 5c show an alternative lower jaw engaging component that is designed to be removable. As shown in the plan view of FIG. 5a, this component includes a moulded body portion 50 which, in use, fits over the teeth of the lower jaw. Abutment projections 51 are formed with the moulded body portion 50 on the inside of the body portion. As shown in the side views of FIGS. 5b and 5c, the moulded body portion 50 may be fixed to the teeth by wire clasps 52 (as in FIG. 5b) or by the moulded body portion 50 itself engaging the side of the teeth (as in FIG. 5c).

When the upper and lower jaw engaging components are fitted to the upper and lower jaws respectively, and the lower jaw is moved to a forward position, any attempt to move the lower jaw backwardly with respect to the upper jaw will cause the shoulders 42a, 42b of the lower jaw engaging component to abut against the free ends 26 of the projections 22 of the upper jaw engaging component, thereby preventing further rearward movement of the lower jaw. Therefore, the appliance provides the essential function of the orthodontic appliance.

Due to the resilience of the projections from the upper jaw engaging component, the user may find it pleasurable to try to move the lower jaw backwards against the resilience of the abutment between the upper and lower jaw engaging components. This is advantageous as this helps to exercise the muscles of the jaw.

Due to the projections being formed as a bent length of wire, it is easy to adjust the device, and in particular to adjust the relative positions of the upper and lower jaw engaging components by simply bending the wire. This has two advantages. Firstly there is no need to precisely form or adjust the appliance based on bite mouldings taken front the patient. Instead, the appliance can be adjusted as this is being fitted to the patient. Further, as it is easy to adjust the device, it is possible to initially set the device to cause a small displacement of the lower jaw, and to adjust this to progressively increase the displacement as the jaw moves towards the correct position.

In an alternative example shown in FIGS. 7 to 10, the abutment between the upper and lower jaw components occurs in the space between the teeth and the check.

The upper jaw engaging component includes a one-piece or two-piece moulding, with a wire 72 depending from the moulding to form projections. These projections are laterally outside the moulding. The upper jaw engaging member may be fixed to the upper jaw using a clasp 70.

Figure 7:
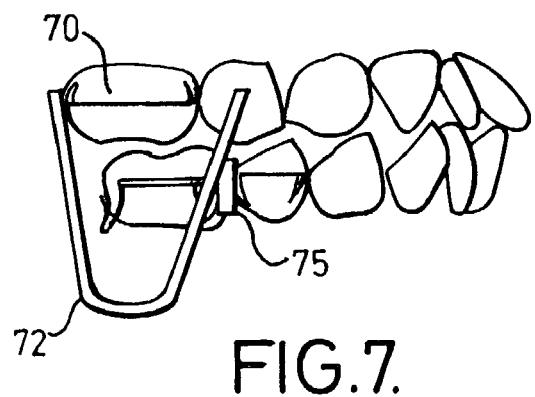
FIG. 7 shows an alternative example of the appliance in use.
Figure 8:
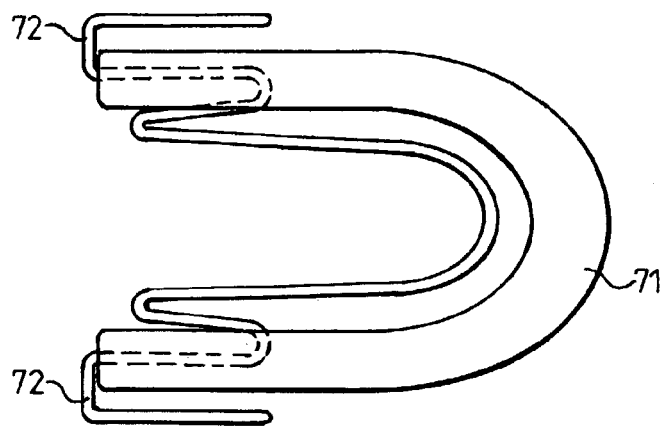
FIG. 8 shows a view from below of the upper jaw engaging component as used in FIG. 7; and, FIGS. 9 and 10 show alternative examples of a lower jaw engaging component as used in the example of FIG. 7.
Figure 9:
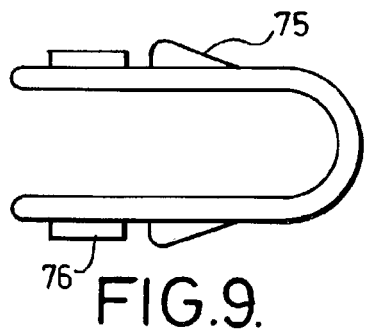
Figure 10:
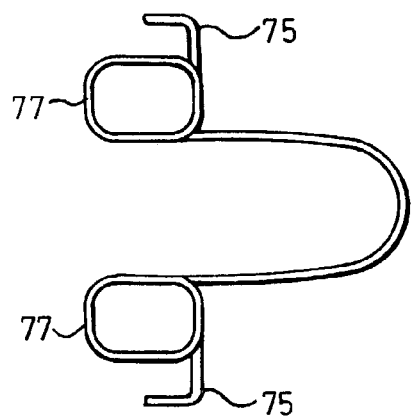

Examples of lower jaw engaging components are shown in FIGS. 9 and 10. FIG. 9 shows a removable component including a moulded portion that fits over the teeth of the lower jaw, and can be fitted to these using a suitable clasp 76. The moulding is provided with a pair of laterally extending shoulders 75 that, in use, abut the projections 72 of the upper jaw engaging component as shown in FIG. 7. FIG. 10 shows a lower jaw engaging component similar to that of FIG. 4 and designed to be fixed to the teeth of the lower jaw by tooth encircling bands 77. Outwardly extending shoulders 75 are provided to engage the projections 72 of the upper jaw engaging component. As an alternative to tooth encircling bands, the lower jaw engaging component may be formed as part of a crown cap.

In addition to its orthodontic function, the appliance of the present invention can have other uses, including use to prevent snoring. In this case, the device holds the lower jaw forward, opening the airway to prevent snoring.

What is claimed is:

1. An orthodontic appliance arranged to hold one of the upper and lower jaws in a forward position, the appliance comprising:
   a first component for engaging the upper jaw;
   a second component for engaging the lower jaw;
   at least one of the first and second components including a wire comprising a central portion and opposed end portions, the opposed end portions defining fixed projections arranged to abut the other of the first and second components, the fixed projections providing an abutment disposed between each of the components, which abutments are offset laterally from the left side and right side of the jaws, respectively, towards the back of the mouth and restrict the relative longitudinal movement of the upper and lower jaw in one direction.

2. The appliance according to claim 1, in which the abutments between the components occur between the outside of the jaw and the inside of the cheek.

3. The appliance according to claim 1, in which the abutments between the components occur between the left and right sides of the jaw.

4. The appliance according to claim 1, in which the wire provided for the abutments between the two components has some resilience.

5. The appliance according to claim 4, in which the wire is or the abutment surfaces are formed of a resilient material.

6. The appliance according to claim 1, in which the wire is bent to provide resilience.

7. The appliance according to claim 1, arranged such that the position of the abutments between the first and second components are adjustable.

8. The appliance according to claim 7, in which the position of the abutments between the upper and lower components are adjustable by displacement of the projections or abutment surfaces.

9. The appliance according to claim 8, in which the wire is selectively connected to the jaw engaging components at one of a plurality of different positions.

10. The appliance according to claim 8, in which the projections are connected to the jaw engaging component by an adjustable interconnection.

11. The appliance according to claim 8, in which the wire is formed from a bendable or otherwise adjustable material.

12. The appliance according to claim 1, in which the wire is formed from stainless steel.

13. The appliance according to claim 1, in which one or both of the jaw engaging components provide an expansive force.

14. The appliance according to claim 13, in which the components are formed from a resilient material.

15. The appliance according to claim 13, in which the expansive force is provided by forming the jaw engaging component in a number of separate pieces, some or all of which are resiliently biased away from each other.

16. The appliance according to claim 15, in which the pieces of the jaw engaging component are resiliently biased away from each other using the wire.

17. The appliance according to claim 13, in which one or both of the jaw engaging components is formed from a plurality of pieces, and at least one spacer to laterally space the pieces from each other.

18. The appliance according to claim 17, in which the spacer includes a threaded component between two of the plurality of pieces.

19. The appliance according to claim 18, in which the spacer includes at least one component threadable along the threaded component and arranged to abut against one of the pieces of the jaw engaging means.

20. The appliance according to claim 18, in which the threaded component is threadable into at least one of the pieces of the jaw engaging means to adjust the spacing between the pieces of the jaw engaging means.

21. The appliance according to claim 1, in which the wire is moulded into the parts forming the jaw engaging component.

22. The appliance according to claim 1, in which at least one of the jaw engaging components includes bands for encircling one or more teeth on the jaw.

23. The appliance according to claim 1, in which at least one or both of the jaw engaging components is removable, allowing the user to remove the appliance.

24. The appliance according to claim 1, in which each of the first and second components engage at least half of the teeth present in the respective upper or lower jaw.

25. A wire for use in an orthodontic appliance, including a first jaw engaging component formed from at least two parts, the wire including a central portion for connecting the at least two parts of the first jaw engaging component, a portion for fixing the wire to the parts of the jaw engaging component, and end portions forming projections, each of which is arranged to extend from the first jaw engaging component to abut a second jaw engaging component.

26. The wire according to claim 25, the wire is formed of stainless steel.

27. The wire according to claim 25, in which the projections are resilient.

28. A method of preventing snoring or correcting malocclusions, comprising providing an appliance having a first component for engaging the upper jaw, and a second component for engaging the lower jaw, one of the first and second components including a wire comprising a central portion and opposed end portions, the opposed end portions defining fixed projections providing an abutment disposed between each of the components, which abutments are offset laterally from the left side and right side of the jaws, respectively, towards the back of the mouth, engaging the first component with the upper jaw, engaging the second component with the lower jaw, and arranging the projections on one of the first and second components to abut the other of the first and second components laterally from the teeth of the jaws to restrict relative longitudinal movement of the upper and lower jaws in one direction.

29. The method according to claim 28, in which the abutments occur between the left and right sides of the jaws.

30. The method according to claim 28, in which the abutments of the components is resilient.

31. The method according to claim 28, in which the relative positions of the first and second components at which they abut is adjustable.

32. The method according to claim 31, in which the relative positions of the first and second components at which they abut is adjusted progressively as the malocclusion is corrected.

33. The method according to claim 28, in which one or both of the jaw engaging components is laterally resilient to apply a lateral spreading force to the upper and/or lower jaw.

34. The method according to claim 33, in which the lateral spreading force is adjusted progressively.

35. The method according to claim 28, in which the abutments occur between the outside of the jaw and the inside of the cheek.

36. An orthodontic appliance arranged to hold one of the upper and lower jaws in a forward position, the appliance comprising:
    a first component for engaging the upper jaw;
    a second component for engaging the lower jaw;
    at least one of the first and second components including
        a fixed projection arranged to abut the other of the first and second components, the fixed projection being arranged so that, in use, the abutment between the components is offset laterally from the left and right side of the jaws towards the back of the mouth and restricts the relative longitudinal movement of the upper and lower jaw in one direction and in which one or both of the jaw engaging components provide an expansive force.

37. The appliance according to claim 36, in which the expansive force is provided by forming the jaw engaging component in a number of separate pieces, some or all of which are resiliently biased away from each other.

38. The appliance according to claim 37, in which the pieces of the jaw engaging component are resiliently biased away from each other using a wire or strip of resilient material.

39. The appliance according to claim 38, in which the wire or strip of resilient material forms the projection.

40. The appliance according to claim 39, in which the wire is moulded into the parts forming the jaw engaging component.

41. The appliance according to claim 36, in which the component is formed from a resilient material.

42. The appliance according to claim 41, in which the resilience is provided by a wire or strip formed of resilient material that also forms the projection.

43. An appliance according to claim 36, in which one or both of the jaw engaging components is formed from a plurality of pieces, and at least one spacer to laterally space the pieces from each other.

44. The appliance according to claim 43, in which the spacer includes a threaded component between two of the plurality of pieces.

45. An appliance according to claim 44, in which the spacer includes at least one component threadable along the threaded component and arranged to abut against one of the pieces of the jaw engaging means.

46. The appliance according to claim 44, in which the threaded component is threadable into at least one of the pieces of the jaw engaging means to adjust the spacing between the pieces of the jaw engaging means.

47. A method of correcting malocclusions, comprising providing an appliance having a first component for engaging the upper jaw, and a second component for engaging the lower jaw, one of the first and second components including a projection, engaging the first component with the upper jaw, engaging the second component with the lower jaw, arranging the projection on one of the first and second components to abut the other of the first and second components laterally from the teeth of the jaws to restrict relative longitudinal movement of the upper and lower jaws in one direction, and progressively adjusting the relative position at which the first and second components abut as the malocclusion is corrected.

48. The method according to claim 47, in which one or both of the jaw engaging components is laterally resilient to apply a lateral spreading force to the upper and/or lower jaw.

49. The method according to claim 48, in which the lateral spreading force is adjusted progressively.

50. A method of correcting malocclusions, comprising providing an appliance having a first component for engaging the upper jaw, and a second component for engaging the lower jaw, one of the first and second components including a projection, engaging the first component with the upper jaw, engaging the second component with the lower jaw, and arranging the projection on one of the first and second components to abut the other of the first and second components laterally from the teeth of the jaws to restrict relative longitudinal movement of the upper and lower jaws in one direction, where one or both of the jaw engaging components is laterally resilient to apply a lateral spreading force to the upper and/or lower jaw.

51. The method according to claim 50, in which the lateral spreading force is adjusted progressively.

52. An orthodontic appliance arranged to hold one of the upper and lower jaws in a forward position, the appliance comprising:
- a first moulding for engaging the upper jaw;
- a second moulding for engaging the lower jaw;
- at least one of the first and second mouldings comprising embedded in it a wire including a pair of projections arranged to abut the other of the first and second mouldings, the fixed projections providing abutments between each of the projections and mouldings, which abutments are offset laterally from the left and right side of the jaws, respectfully, towards the back of the mouth between the left and right sides of the jaw and restrict the relative longitudinal movement of the upper and lower jaw in one direction.

* * * * *